US012415839B2

(12) United States Patent
Lunder et al.

(10) Patent No.: US 12,415,839 B2
(45) Date of Patent: Sep. 16, 2025

(54) IgE EPITOPE-LIKE PEPTIDES AND USES THEREOF

(71) Applicants: Univerza v Ljubljani, Ljubljana (SI); University Clinic of Respiratory and Allergic Diseases Golnik, Golnik (SI)

(72) Inventors: Mojca Lunder, Ljubljana (SI); Borut Štrukelj, Ljubljana (SI); Peter Korošec, Ljubljana (SI); Ana Koren, Ljubljana (SI); Jernej Luzar, Ljubljana-Črnuče (SI); Abida Zahirović, Sarajevo (SI)

(73) Assignees: Univerza v Ljubjani, Ljubljana (SI); University Clinic of Respiratory and Allergic Diseases, Golnik (SI)

( * ) Notice: Subject to any disclaimer, the term of this patent is extended or adjusted under 35 U.S.C. 154(b) by 1332 days.

(21) Appl. No.: 17/058,367

(22) PCT Filed: May 29, 2018

(86) PCT No.: PCT/EP2018/064063
§ 371 (c)(1),
(2) Date: Nov. 24, 2020

(87) PCT Pub. No.: WO2019/228612
PCT Pub. Date: Dec. 5, 2019

(65) Prior Publication Data
US 2021/0115097 A1    Apr. 22, 2021

(51) Int. Cl.
*C07K 7/08* (2006.01)
*A61K 9/00* (2006.01)
*A61K 38/00* (2006.01)
*A61K 39/35* (2006.01)
*A61P 37/08* (2006.01)
*C07K 14/415* (2006.01)
*A61K 39/00* (2006.01)

(52) U.S. Cl.
CPC .......... *C07K 14/415* (2013.01); *A61K 9/0019* (2013.01); *A61K 9/0053* (2013.01); *A61K 39/35* (2013.01); *A61P 37/08* (2018.01); *A61K 38/00* (2013.01); *A61K 2039/577* (2013.01)

(58) Field of Classification Search
None
See application file for complete search history.

(56) References Cited

U.S. PATENT DOCUMENTS

2017/0290341 A1*  10/2017  Cordova-Kreylos ........................ C12N 9/2442

OTHER PUBLICATIONS

Gray C.L. (2020) Journal of Asthma and Allergy 13: 51-66.*

Communication pursuant to Article 94(3) EPC dated Nov. 14, 2023, for European Patent Application No. 18731365.5.
Jernej Luzar et al.; Doktorska Disertacija; Jan. 1, 2016; XP93098943.
Calderon et al., Clinical and Translational Allergy 2012, 2:20, http://www.ctajournal.com/content/2/1/20, EAACI: A European Declaration on Immunotherapy. Designing the future of allergen specific immunotherapy.
S. Allan Bock, Md, et al., Fatalities due to to anaphylactic reactions to foods, Jan. 2001.
Asarnoj A. et al., IgE to peanut allergen compo-nents: relation to peanut symptoms and pollen sensitization in 8-year-olds. Allergy 2010; 65: 1189-1195.
Akdis World Allergy Organization Journal 2014, 7:23 http://www.waojournal.org/content/7/1/23, New treatments for allergen immunotherapy.
Berings M. et al., Advances and Highlights in Allergen Immunotherapy: On the way to sustained clinical and immunologic tolerance, Journal of Allergy and Clinical Immunology (2017), doi: 10.1016/j.jaci.2017.08.025.
Saul B. Needleman et al, A General Method Applicable to the Search for Similarities in the Amino Acid Sequence of Two Proteins, J. Mol. Biol. 48, 443-453, 1970.
Linhart et al., Mechanisms underlying allergy vaccination with recombinant hypoallergenic allergen derivatives, journal homepage: www.elsevier.com/locate/vaccine, Vaccine 30, 4328-4335 2012.
Valenta et al., Recombinant allergy vaccines based on allergen-derived B cell epitopes, Immunol Lett. Sep. 2017 ; 189: 19-26. doi:10.1016/j.imlet.2017.04.015.
Carolin Cornelius et al., Immunotherapy With the PreS-based Grass Pollen Allergy Vaccine BM32 Induces Antibody Responses Protecting Against Hepatitis B Infection, EBioMedicine 11 (2016) 58-67.
Mark Larche, Current Topics in Microbiology and Immunology (2011) 352: 107-119 DOI: 10.1007/82_2011_131, Springer-Verlag Berlin Heidelberg 2011 Published Online: May 13, 2011.
William R. Pearson et al., Improved tools for biological sequence comparison, Proc. Natl. Acad. Sci. USA vol. 85, pp. 2444-2448, Apr. 1988.
Temple F. Smith et al., Comparison of Biosequences, Advances in Applied Mathematics 2, 482-489, 1981.
Yael Gernez, Md et al., Immunotherapy for Food Allergy: Are We There Yet?, Clinical Commentary Review, 2017.
Susan L. Prescott et al., A global survey of changing patterns of food allergy burden in children, Prescott et al. World Allergy Organization Journal 2013, 6:21 http://www.waojournal.org/content/.
Moradi et al., Glycosylation, an effective synthetic strategy to improve the bioavailability of therapeutic peptides, Chem. Sci., 7, 2492, 2016.

(Continued)

*Primary Examiner* — Ilia I Ouspenski
(74) *Attorney, Agent, or Firm* — Renner, Otto, Boisselle & Sklar, LLP

(57) ABSTRACT

The present invention relates to IgE epitope-like peptides which have ability to bind to allergen specific IgE paratopes. Said allergen specific IgEs are bound to effector cells of allergic patients. The IgE epitope-like peptides of the invention cover the paratopes of said IgE bound on effector cells, prevent biding of causative allergen on said IgE on effector cells, and thereby prevent degranulation and secretion of mediators of allergic inflammation from effector cells, after contact with the causative allergen. The present invention relates to the methods of using such IgE epitope-like peptides for therapy of allergic reaction. Said allergic reaction is caused by exposure to the causative allergen.

1 Claim, 5 Drawing Sheets
Specification includes a Sequence Listing.

(56) References Cited

OTHER PUBLICATIONS

MacGinnitie et al., Omalizumab facilitates rapid oral desensitization for peanut allergy, J Allergy Clin Immunol. Mar. 2017; 139(3): 873-881.e8. doi: 10.1016/j.jaci.2016.08.010., Mar. 1, 2018.
Chen X et al: Conformational IgE epitopes of peanut allergens Ara h 2 and Ara h 6 II' Clinical and Experimental Allergy, vol. 46, No. 8, Aug. 2016 (2016-08), pp. 1120-1128, XP002787960, abstract p. 1123; figure 1—p. 1123, left-hand column, p. 1124, left-hand column, paragraph 3 p. 1122, left-hand column, paragraph 2.
Luzar Jet al: Phage display peptide libraries in molecular allergology: from epitope mapping to mimotope-based immunotherapy11, Allergy (Oxford), vol. 71, No. 11, Nov. 2016 (Nov. 2016), pp. 1526-1532, XP002787961, the whole document.
Uzar Jernej et, Identification characterization of major cat allergen Fel d 1 mimotopes on filamentous phage carriers 11, Molecular Immunology, Pergamon, GB, vol. 71, Feb. 21, 2016 (Feb. 21, 2016), pp. 176-183, XP029444988, ISSN: 0161-5890, DOI: 10.1016/J.MOLIMM.2016.02.004 abstract p. 177, left-hand column, paragraph 5—right-hand column, paragraph 2 p. 183, left-hand column, paragraph 1.
Luzar J et al: The major peanut allergen Ara h 2 mimotopes: identification, characterization and display on Lactococcus lactis11, Allergy (Oxford), vol. 71, No. Suppl. 102, Sp. I s s . SI, Aug. 2016 (Aug. 2016), pp. 91-92, XP009510454, & Annual Congress of the European-Academy-of-Allergy-and-Clinical-Immunology; Vienna, Austria; Jun. 11-15, 2016 p. 92, middle column-right-hand column.
Uzar Jet al: "Peptide Mimotopes Ofallergens in Immunotherapy", Journal of Peptide Science, vol. 22, No. Suppl. S2, Sep. 2016 (Sep. 2016), p. S178, XP009510455, & 34th European Peptide Symposium; Leipzig, Germany; Sep. 4-9, 2016 the whole document.
Michael J. Hackett et al., Fatty acids as therapeutic auxiliaries for oral and parenteral formulations, Advanced Drug Delivery Reviews 65, 1331-1339, 2013.
R. Valenta et al., Allergen-specific immunotherapy: from therapeutic vaccines to prophylactic approaches, J Intern Med. Aug. 2012; 272(2): 144-157. doi:10.1111/j.1365-2796.2012.02556.x.

* cited by examiner

A

| SEQ ID NO | Peptide name | Amino acid sequence |
|---|---|---|
| 1 | ELP 1 | DHPRFNDSYNSP |
| 2 | ELP 2 | DHPRFNRDNDVA |
| 3 | ELP 3 | DHPRFNYVSQPW |
| 4 | ELP 4 | DHPRFAP |
| 5 | ELP 5 | DHPRYGP |
| 6 | ELP 6 | DHPRFST |
| 7 | ELP 7 | DHPRFAE |
| 8 | ELP 8 | DHPRFPL |
| 9 | ELP 9 | DHPRFSF |
| 10 | ELP 10 | NHPRFNL |

B

Z-$X^1$-His-Pro-Arg-$X^2$- $X^3$- $X^4$- $X^5$- $X^6$- $X^7$- $X^8$- $X^9$-U $X^1$ is Asp or Asn $X^2$ is Phe or Tyr $X^3$ may or may not be present but when present it is Asn, Ala, Gly, Ser or Pro $X^4$ may or may not be present but when present it is Asp, Arg, Tyr, Pro, Thr, Glu, Leu or Phe $X^5$ may or may not be present but if present it is Ser, Asp or Val $X^6$ may or may not be present but if present it is Tyr, Ser or Asn $X^7$ may or may not be present but if present it is Gln, Asn or Asp $X^8$ may or may not be present but if present it is Ser, Val or Pro $X^9$ may or may not be present but if present it is Ala, Trp or Pro Z - may or may not be present, but when present Z is a stability enhancing moiety U may or may not be present, but when present U is a stability enhancing moiet

Figure 1

A
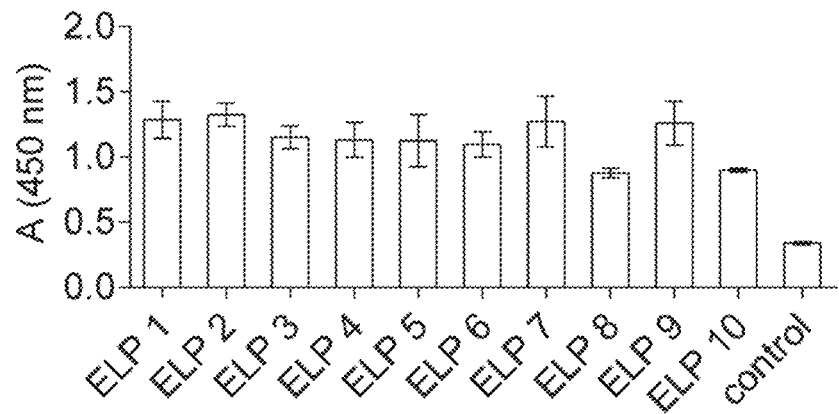
B
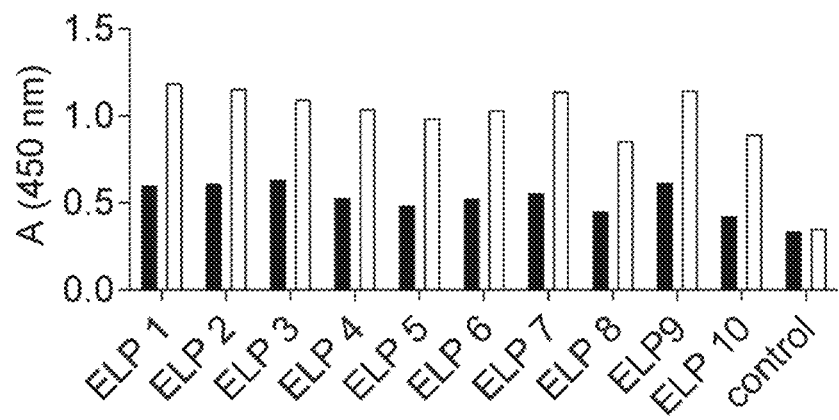
Figure 2

SEQUENCE LISTING

<160> NUMBER OF SEQ ID NOS: 10

<210> SEQ ID NO 1
<211> LENGTH: 12
<212> TYPE: PRT
<213> ORGANISM: Artificial Sequence
<220> FEATURE:
<223> OTHER INFORMATION: IgE epitope-like peptide

<400> SEQUENCE: 1

Asp His Pro Arg Phe Asn Asp Ser Tyr Asn Ser Pro
1               5                   10

<210> SEQ ID NO 2
<211> LENGTH: 12
<212> TYPE: PRT
<213> ORGANISM: Artificial Sequence
<220> FEATURE:
<223> OTHER INFORMATION: IgE epitope-like peptide

<400> SEQUENCE: 2

Asp His Pro Arg Phe Asn Arg Asp Asn Asp Val Ala
1               5                   10

<210> SEQ ID NO 3
<211> LENGTH: 12
<212> TYPE: PRT
<213> ORGANISM: Artificial Sequence
<220> FEATURE:
<223> OTHER INFORMATION: IgE epitope-like peptide

<400> SEQUENCE: 3

Asp His Pro Arg Phe Asn Tyr Val Ser Gln Pro Trp
1               5                   10

<210> SEQ ID NO 4
<211> LENGTH: 7
<212> TYPE: PRT
<213> ORGANISM: Artificial Sequence
<220> FEATURE:
<223> OTHER INFORMATION: IgE epitope-like peptide

<400> SEQUENCE: 4

Asp His Pro Arg Phe Ala Pro
1               5

<210> SEQ ID NO 5
<211> LENGTH: 7
<212> TYPE: PRT
<213> ORGANISM: Artificial Sequence
<220> FEATURE:
<223> OTHER INFORMATION: IgE epitope-like peptide

<400> SEQUENCE: 5

Asp His Pro Arg Tyr Gly Pro
1               5

<210> SEQ ID NO 6
<211> LENGTH: 7
<212> TYPE: PRT
<213> ORGANISM: Artificial Sequence
<220> FEATURE:
<223> OTHER INFORMATION: IgE epitope-like peptide

<400> SEQUENCE: 6

Asp His Pro Arg Phe Ser Thr
1               5

```
<210> SEQ ID NO 7
<211> LENGTH: 7
<212> TYPE: PRT
<213> ORGANISM: Artificial Sequence
<220> FEATURE:
<223> OTHER INFORMATION: IgE epitope-like peptide

<400> SEQUENCE: 7

Asp His Pro Arg Phe Ala Glu
1               5

<210> SEQ ID NO 8
<211> LENGTH: 7
<212> TYPE: PRT
<213> ORGANISM: Artificial Sequence
<220> FEATURE:
<223> OTHER INFORMATION: IgE epitope-like peptide

<400> SEQUENCE: 8

Asp His Pro Arg Phe Pro Leu
1               5

<210> SEQ ID NO 9
<211> LENGTH: 7
<212> TYPE: PRT
<213> ORGANISM: Artificial Sequence
<220> FEATURE:
<223> OTHER INFORMATION: IgE epitope-like peptide

<400> SEQUENCE: 9

Asp His Pro Arg Phe Ser Phe
1               5

<210> SEQ ID NO 10
<211> LENGTH: 7
<212> TYPE: PRT
<213> ORGANISM: Artificial Sequence
<220> FEATURE:
<223> OTHER INFORMATION: IgE epitope-like peptide

<400> SEQUENCE: 10

Asn His Pro Arg Phe Asn Leu
1               5
```

IgE EPITOPE-LIKE PEPTIDES AND USES THEREOF

This application is a national phase of International Application No. PCT/EP2018/064063 filed May 29, 2018 and published in the English language, which is hereby incorporated herein by reference.

FIELD OF THE INVENTION

The present invention relates to IgE epitope-like peptides which have ability to bind to allergen specific IgE paratopes. Said allergen specific IgEs are bound to effector cells of allergic patients. The IgE epitope-like peptides of the invention cover the paratopes of said IgE bound on effector cells, prevent biding of causative allergen on said IgE on effector cells, and thereby prevent degranulation and secretion of mediators of allergic inflammation from effector cells, after contact with the causative allergen. The present invention relates to the methods of using such IgE epitope-like peptides for therapy of allergic reaction. Said allergic reaction is caused by exposure to the causative allergen.

BACKGROUND

With a current estimate of more than 150 million patients and a prediction of more than 300 million in Europe in the next decade (Calderon et al., 2012), allergies constitute a public health concern of pandemic proportions. Type I allergy is characterized by production of immunoglobulin E (IgE) antibodies against per se harmless antigens-allergens. A subsequent contact with allergen then leads to cross-linking of effector cells (mast cells and basophils) bound IgE which results in degranulation and secretion of mediators of allergic inflammation that trigger symptoms like rhinitis, conjunctivitis, atopic dermatitis, exacerbation of allergic asthma, and in severe cases, potentially life-treating anaphylaxis. Activation of these cells further leads to consecutive release of cytokines and/or presentation of allergen to specific T cells which can cause a late phase allergic inflammation. Allergen specific IgE response of effector cells is therefore crucial for the development of allergic symptoms in sensitized patients. The most life-threatening IgE-mediated allergy is allergy to peanuts. In fact, ⅔ of deaths caused by anaphylaxis in the USA are a consequence of peanut intake (Bock et al., 2001). Peanut allergy is affecting almost 2% of children in the UK, the USA, and Canada (Prescott et al., 2013) and 80-85% of peanut allergic patients develop specific IgE against major peanut allergen Ara h 2 (Asarnoj et al., 2010).

Allergen-specific immunotherapy (AIT) by the administration of increasing doses of allergen extracts remains the single curative approach with the potential to induce specific immune tolerance and yield long term disease modifying effect. AIT is based on the use of crude allergen extracts. They contain a variety of allergenic and non-allergenic components and are difficult to standardize. Their use unpredictably evokes de novo IgE sensitization to previously non-reactive allergen components and most importantly is associated with allergic adverse events, ranging from local to life treating anaphylactic reactions, which are limiting its applicability (Akdis, 2014). Conventional subcutaneous AIT is associated with the need for frequent injections over minimally 3 years, with the risk of systemic adverse events including anaphylaxis. Sublingual AIT allows self-administration, however it requires daily intake for 3 year. New AIT approaches are constantly being developed. Besides alternative routes of administration (intradermal, epicutaneous, intralymphatic, oral, nasal) new strategies include purified (wild type) or recombinant allergens, recombinant hypoallergenic allergens and allergen peptides (Berings et al., 2017).

Using recombinant expression and synthetic peptide chemistry it has become possible to produce allergen-derivatives with defined immunological properties for possible use in AIT (Valenta et al., 2012). Upon AIT administration, recombinant allergens, which resemble the epitope spectrum of the natural allergens, stimulate allergen-specific IgE, IgG and T cell responses and therefore similar as natural allergens often induce unwanted adverse events. The term "hypoallergen" defines an allergen derivative which has been modified to exhibit reduced IgE reactivity and allergenic activity, and therefore demonstrate reduced capability to induce allergic adverse events. Hypoallergens that are made to preserve the T cell epitope repertoire of the corresponding natural allergen, are often bound to different carriers and upon administration preferably induce allergen-specific IgG antibodies (Linhart and Valenta, 2012). Further development of hypoallergen AIT concept include B cell-epitope-peptides, which are also bound to a carrier. Those B cell-epitope hypoallergens induce B-cell production of blocking allergen-specific IgG antibodies, similar as natural allergens, but again with very limited induction of IgE response (Valenta et al., 2017). In addition, B cell-epitope carriers also enhance allergen-specific T cell response (Cornelius et al., 2016). Another development of hypoallergen AIT concept include allergen-derived T cell epitopes. They are often made by synthetic peptide chemistry to resemble allergen-specific T cell epitopes of the natural allergens, but show no IgE reactivity. T cell epitope-containing peptides can target allergen-specific T cells, without induction of allergen-specific IgG or IgE responses. The lack of induction of allergen-specific IgG responses may have been responsible for clinical inefficiency of allergen-derived T cell epitopes (Larche, 2011). Overall, immunological mechanisms of treatment with hypoallergens is comparable with natural allergens (induction of blocking IgG antibodies and T cell tolerance), however they can be considered as more safe compared to natural allergens because of their reduced IgE reactivity and allergenic activity and thus reduced ability to induce allergic adverse events.

Peanut and tree nut allergy is considered a significant public health concern, affecting more than 3% of children in the developed world. Peanut allergy remains the leading cause of fatal anaphylactic reactions.

Management of peanut anaphylaxis currently includes only treatment of symptoms during a reaction and strict dietary avoidance and education on potential situations, which may place the patient at high risk for accidental exposure. Strict dietary avoidance is considerable limited with cross-reactivity between various nuts along with various cross-contamination sources. The biochemical and immunologic studies of peanut allergens demonstrated that 4 peanut allergens, Ara h 1 and Ara h 3, which belong to the cupin superfamily, and Ara h 2 and Ara h 6, which belong to the 2S albumin family, have potential for induction of serious allergic reactions to peanut. Comparing the functional activities by using skin and basophil activation tests showed that these allergens were active in terms of their capacities of cross-linking IgE and inducing skin reactions of mast cells and basophil degranulation. However, Ara h 2 is pre-eminent in importance because it was identified as a predictor of clinical reactivity to peanut and more potent in degranulating basophils than Ara h 1 and Ara h 3. Thus highor very high-titer IgE antibodies for Ara h 2 characterize severe peanut allergy. In addition occurrence of similar sequences Ara h 1 and 3 accounts for the high extent of cross-reactivity with Ara h 2. Approximately one-third of patients with peanut allergy report clinical reactivity to tree nuts, the reason is cross-reactivity between peanut and certain tree nut epitopes (almond, walnut, pecan, hazelnut, Brazil nut).

AIT is significantly limited in food allergy and especially in the case of peanut allergy. Due to severe systemic adverse events (mainly anaphylactic reactions) and low efficiency, peanut AIT is not in clinical practice. There are no currently approved therapies, although 2 commercial products (peanut AR101 by Aimmune Therapeutics [Brisbane, Calif] and Viaskin Peanut by DBV Technologies [Montrouge, France]) are in the phase III clinical trials. However, none of these immunotherapeutic approaches have been proven to deliver a permanent cure of peanut allergy (Gernez and Nowak-Wegrzyn, 2017). Furthermore, there are currently no peanut hypoallergen treatment possibilities or clinical trial. The combination of peanut AIT with monoclonal antibodies to IgE (Omalizumab) has also been tested with moderate results and aim to increase tolerability, efficacy, and reduce the time needed for up-dosing (MacGinnitie et al., 2017). Obviously novel approaches are needed for treatment of peanut allergic patients.

Here we disclose a new therapeutic and prophylactic strategy for treatment of type I allergies, more specifically for treatment of peanut allergy. The mechanism of the IgE epitope-like peptides of the invention does not induce blocking IgG antibodies and/or T cell tolerance, as described for AIT. The IgE epitope-like peptides inhibit activation of effector cell by causative allergen and prevent allergic reaction to causative allergen. Thereby, they represent a novel therapy for peanut allergy. This novel therapy could also substitute monoclonal antibody against IgE (Omalizumab) for prevention of systemic adverse events during AIT with peanut allergen and for prevention of allergic reaction during medical interventions with peanut allergen or peanut extracts.

SUMMARY OF THE INVENTION

The present invention addresses a novel peanut allergy therapy by providing IgE epitope-like peptides. The IgE epitope-like peptides of the invention bind to peanut specific IgEs and Ara h 2 specific IgEs on the surface of effector cells (mast cells and basophils) of peanut allergic patients. The IgE epitope-like peptides prevent cross-linking of said IgE by the causative allergen and thereby prevent degranulation and secretion of mediators of allergic inflammation from said effector cells, by the causative allergen. The present invention further relates to the pharmaceutical compositions comprising IgE epitope-like peptides and methods of using such compositions for therapy of allergy to nuts, preferably peanuts.

Additionally the invention describes a general method of using IgE epitope-like peptides for treatment of allergic patients, where IgE epitope-like peptides prevent cross-linking of allergen specific IgE and thereby prevent that causative allergen induce effector cell activation and secretion of mediators of allergic inflammation.

IgE epitope-like peptides are peptides derived from allergen structure. In a preferred embodiment IgE epitope-like peptides are derived from major peanut allergen Ara h 2. Preferably, IgE epitope-like peptides mimic immunodominant epitopes of Ara h 2, located between helices 2 and 3 in the three-dimensional structure of Ara h 2.

Specifically, the present invention encompasses the following items [1] to [96].

[1] An IgE epitope-like peptide having the following structure:

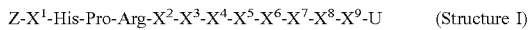

$$Z\text{-}X^1\text{-His-Pro-Arg-}X^2\text{-}X^3\text{-}X^4\text{-}X^5\text{-}X^6\text{-}X^7\text{-}X^8\text{-}X^9\text{-}U \qquad \text{(Structure I)}$$

wherein $X^1$ is a polar or charged amino acid, preferably Asp or Asn; $X^2$ s a hydrophobic, aromatic amino acid, preferably Phe or Tyr; $X^3$ may or may not be present, but if present it is a polar or non-polar amino acid, preferably Asn, Ala, Gly, Ser or Pro; $X^4$ may or may not be present, but if present it can be any amino acid, preferably Asp, Arg, Tyr, Pro, Thr, Glu, Leu or Phe; $X^5$ may or may not be present, but if present it is preferably a charged or polar amino acid, and more preferably Ser, Asp or Val; $X^6$ may or may not be present, but if present it is a polar amino acid, preferably Tyr, Ser or Asn; $X^7$ may or may not be present, but if present it is a polar or charged amino acid, preferably Gln, Asn or Asp; $X^8$ may or may not be present, but if present it is a non-polar or polar amino acid, preferably Val, Pro or Ser; $X^9$ may or may not be present, but if present it is a non-polar amino acid, preferably Ala, Trp or Pro; Z is a hydrogen atom replacing the N-terminal amino group or an N-terminal amino group, or a stability enhancing moiety, bound either to the N-terminal amino group or directly to the alpha C-atom of the N-terminal residue; U is a hydrogen atom replacing the C-terminal carboxyl group or a C-terminal carboxyl group, or is a linker or a stability enhancing moiety, bound either to the C-terminal carbonyl group or directly to the alpha C-atom of the C-terminal residue.

[2] The peptide of item [1], wherein $X^1$ is Asp or Asn.
[3] The peptide of item [1], wherein $X^1$ is Asp.
[4] The peptide of item [1], wherein $X^1$ is Asn.
[6] The peptide of any one of items [1] to [4], wherein $X^2$ is Phe or Tyr.
[7] The peptide of any one of items [1] to [4], wherein $X^2$ is Phe.
[8] The peptide of any one of items [1] to [4], wherein $X^2$ is Tyr.
[9] The peptide of any one of items [1] to [8], wherein $X^3$ is not present.
[10] The peptide of any one of items [1] to [8], wherein $X^3$ is present
[11] The peptide of item [10], wherein $X^3$ is Asn, Ala, Gly, Ser or Pro.
[12] The peptide of item [10], wherein $X^3$ is Asn.
[13] The peptide of item [10], wherein $X^3$ is Ala.
[14] The peptide of item [10], wherein $X^3$ is Gly.
[15] The peptide of item [10], wherein $X^3$ is Ser.
[16] The peptide of item [10], wherein $X^3$ is Pro.
[17] The peptide of any one of items [1] to [16], wherein $X^4$ is not present.
[18] The peptide of any one of items [1] to [16], wherein $X^4$ is present.
[19] The peptide of item [18], wherein $X^4$ is Asp, Arg, Tyr, Pro, Thr, Glu, Leu or Phe.
[20] The peptide of item [18], wherein $X^4$ is Asp.
[21] The peptide of item [18], wherein $X^4$ is Arg.
[22] The peptide of item [18], wherein $X^4$ is Tyr.
[23] The peptide of item [18], wherein $X^4$ is Pro.
[24] The peptide of item [18], wherein $X^4$ is Thr.
[25] The peptide of item [18], wherein $X^4$ is Glu.
[26] The peptide of item [18], wherein $X^4$ is Leu.
[27] The peptide of item [18], wherein $X^4$ is Phe.

[28] The peptide of any one of items [1] to [27], wherein $X^5$ is not present.

[29] The peptide of any one of items [1] to [27], wherein $X^5$ is present.

[30] The peptide of item [29], wherein $X^5$ is Ser, Asp or Val.

[31] The peptide of item [29], wherein $X^5$ is Ser.

[32] The peptide of item [29], wherein $X^5$ is Asp.

[33] The peptide of item [29], wherein $X^5$ is Val.

[34] The peptide of any one of items [1] to [33], wherein $X^6$ is not present.

[35] The peptide of any one of items [1] to [33], wherein $X^6$ is present.

[36] The peptide of item [35], wherein $X^6$ is Tyr, Ser or Asn.

[37] The peptide of item [35], wherein $X^6$ is Tyr.

[38] The peptide of item [35], wherein $X^6$ is Ser.

[39] The peptide of item [35], wherein $X^6$ is Asn.

[40] The peptide of any one of items [1] to [39], wherein $X^7$ is not present.

[41] The peptide of any one of items [1] to [39], wherein $X^7$ is present.

[42] The peptide of item [41], wherein $X^7$ is Gln, Asn or Asp.

[43] The peptide of item [41], wherein $X^7$ is Gln.

[44] The peptide of item [41], wherein $X^7$ is Asn.

[45] The peptide of item [41], wherein $X^7$ is Asp.

[46] The peptide of any one of items [1] to [45], wherein $X^8$ is not present.

[47] The peptide of any one of items [1] to [45], wherein $X^8$ is present.

[48] The peptide of item [47], wherein $X^8$ is Val, Pro or Ser.

[49] The peptide of item [47], wherein $X^8$ is Val.

[50] The peptide of item [47], wherein $X^8$ is Pro.

[51] The peptide of item [47], wherein $X^8$ is Ser.

[52] The peptide of any one of items [1] to [51], wherein $X^9$ is not present.

[53] The peptide of any one of items [1] to [51], wherein $X^9$ is present.

[54] The peptide of item [53], wherein $X^9$ is Ala, Pro or Trp.

[55] The peptide of item [53], wherein $X^9$ is Ala.

[56] The peptide of item [53], wherein $X^9$ is Pro.

[57] The peptide of item [53], wherein $X^9$ is Trp.

[58] The peptide of any one of items [1] to [57], wherein Z is a hydrogen atom replacing the N-terminal amino group.

[59] The peptide of any one of items [1] to [57], wherein Z is an N-terminal amino group.

[60] The peptide of any one of items [1] to [57], wherein Z is a stability enhancing moiety, bound either to the N-terminal amino group or directly to the alpha C-atom of the N-terminal residue.

[61] The peptide of any one of items [1] to [60], wherein U is a hydrogen atom replacing the C-terminal carboxyl group.

[62] The peptide of any one of items [1] to [60], wherein U is a C-terminal carboxyl group.

[63] The peptide of any one of items [1] to [60], wherein U is a stability enhancing moiety, bound either to the C-terminal carbonyl group or directly to the alpha C-atom of the C-terminal residue.

[64] The peptide of any one of items [1] to [63], wherein one or more amino acids of said peptide are in L-form or D-form, or wherein the amino acids of said peptide are a combination of both L- and D-forms.

[65] The peptide of any one of items [1] to [63], wherein one or more amino acids of said peptide are in L-form.

[66] The peptide of any one of items [1] to [63], wherein one or more amino acids of said peptide are in D-form.

[67] The peptide of any one of items [1] to [63], wherein the amino acids of said peptide are a combination of both L- and D-forms.

[68] The peptide of any one of items [1] to [67], wherein said peptide comprises an amino acid sequence having at least 60%, such as at least 70%, sequence identity with any one of the amino acid sequences SEQ ID NO: 1 to SEQ ID NO: 10.

[69] The peptide of item [68], wherein one or more (such as two or more) amino acids in the reference sequence SEQ ID NO: 1 to SEQ ID NO: 10 are substituted by conservative substitutions.

[70] The peptide of any one of items [1] to [68], wherein said peptide comprises any one of the amino acid sequences SEQ ID NO: 1 to SEQ ID NO: 10.

[71] The peptide of any one of items [1] to [68], wherein said peptide consists of any one of the amino acid sequences SEQ ID NO: 1 to SEQ ID NO: 10.

[72] The peptide of any one of items [1] to [71], wherein said peptide binds to peanut and Ara h 2 specific IgEs of peanut allergic patients.

[73] The peptide of any one of items [1] to [71], wherein said peptide prevents cross-linking of said IgE.

[74] The peptide of any one of items [1] to [71], wherein said peptide prevents degranulation and secretion of mediators of allergic inflammation from effector cells of allergic patients, after contact with the causative allergen.

[75] A retro-inverso analogue of the peptide of any one of items [1] to [71].

[76] A peptidomimetic of the peptide of any one of items [1] to [71].

[77] The peptidomimetic of item [76], wherein one or more amino acids of the ligand are replaced by a non-standard (non-proteinogenic) amino acid other than D-amino acids.

[78] The peptidomimetic of item [76] or [77], comprising a methyl group on one or more nitrogen atoms of the peptide backbone.

[79] The peptidomimetic of any one of items [76] to [78], comprising phosphonate, amidate, carbamate ester or sulphonamide backbone linkages replacing the peptide backbone linkages but retaining the sequences of side chains of the ligand.

[80] The retro-inverso analogue of items [75] or peptidomimetic of any one of items [76] to [79], wherein said analogue or peptidomimetic binds to peanut and Ara h 2 specific IgEs of peanut allergic patients.

[81] The retro-inverso analogue of items [75] or peptidomimetic of any one of items [76] to [79], wherein said analogue or peptidomimetic prevents cross-linking of said IgE.

[82] The retro-inverso analogue of items [75] or peptidomimetic of any one of items [76] to [79], wherein said analogue or peptidomimetic prevents degranulation and secretion of mediators of allergic inflammation from effector cells of allergic patients, after contact with the causative allergen.

[83] The IgE epitope-like peptide of any of items [1] to [74], the retro-inverso analogue of item [75] or the peptidomimetic of any one of items [76] to [79] for use in therapy, preferably for use in therapy of an allergic reaction, and more preferably for use in the treatment of peanut allergy.

[84] The IgE epitope-like peptide of any of items [1] to [74], the retro-inverso analogue of item [75] or the peptidomimetic of any one of items [76] to [79] for use in the treatment of peanut allergy, for prevention of systemic adverse events during peanut immunotherapy or for prevention of allergic reaction during medical interventions with peanut allergens or peanut extracts.

[85] The IgE epitope-like peptide of any of items [1] to [74], the retro-inverso analogue of item [75] or the peptidomimetic of any one of items [76] to [79] for use in the treatment of peanut cross-reactive allergies, for prevention of systemic adverse events during cross-reactive nut immunotherapy or for prevention of allergic reaction during medical interventions with cross reactive allergens or allergen extracts.

[86] A pharmaceutical composition comprising the peptide of any one of items [1] to [74], the retro-inverso analogue of items [75] or peptidomimetic of any one of items [76] to [79], and optionally at least one pharmaceutically acceptable excipient.

[87] The pharmaceutical composition according to item [86], wherein said composition is adapted for any of the following routes of administration: oral administration, intramuscular injection, subcutaneous injection, intradermal injection, intravenous injection, intravenous infusion.

[88] A method for treatment of peanut allergy, said method comprising administering a therapeutic effective amount of the pharmaceutical composition according to item [86] or [87] to a patient in need thereof.

[89] A method for prevention of systemic adverse events during peanut immunotherapy, said method comprising administering a therapeutic effective amount of the pharmaceutical composition according to item [86] or [87] to a patient in need thereof.

[90] A method for prevention of allergic reaction during medical interventions with peanut allergen or peanut extracts, said method comprising administering a therapeutic effective amount of the pharmaceutical composition according to item [86] or [87] to a patient in need thereof.

[91] A method for treatment of peanut cross-reactive allergies, said method comprising administering a therapeutic effective amount of the pharmaceutical composition according to item [86] or [87] to a patient in need thereof.

[92] A method for prevention of systemic adverse events during cross-reactive nut immunotherapy, said method comprising administering a therapeutic effective amount of the pharmaceutical composition according to item [86] or [87] to a patient in need thereof.

[93] A method for prevention of allergic reaction during medical interventions with cross reactive allergens or allergen extracts, said method comprising administering a therapeutic effective amount of the pharmaceutical composition according to item [86] or [87] to a patient in need thereof.

[94] An IgE epitope-like peptide that binds to antigen-binding site of allergen specific IgEs, does not cross-link allergen specific IgEs on effector cells of allergic patients and/or does not induce activation and release of mediators of allergic inflammation from effector cells.

[95] The IgE epitope-like peptide of item [94] that inhibits causative allergen induced effector cell activation in allergic patients.

[96] A method of using an IgE epitope-like peptide of item [94] or [95] in the treatment of clinically relevant allergies, for prevention of systemic adverse reactions during specific immunotherapy and for prevention of allergic reaction during medical interventions.

The present invention is explained in details in the following Sections.

Definitions

As used herein, the following terms have the meanings ascribed to them unless specified otherwise.

The terms "a," "an", or "the" as used herein not only include aspects with one member, but also include aspects with more than one member. For example, the singular forms "a," "an", and "the" include plural referents unless the context clearly dictates otherwise. Thus, for example, reference to "a cell" includes a plurality of such cells and reference to "antibody" includes reference to more antibodies known to those skilled in the art, and so forth.

The term "peptide" or "polypeptide" refers to a polymer of amino acid residues. The term applies to amino acid polymers composed of naturally occurring amino acids (proteinogenic) as well as to polymers where one or more amino acid residue is a non-naturally occurring (non-proteinogenic) amino acid.

As used herein, the terms "peptide" or "polypeptide" encompass amino acid chains of any length from 2 to 100 amino acids, preferably from 2 to 50 amino acids, more preferably from 2 to 12 amino acids, wherein the amino acid residues are linked by covalent peptide bonds.

By "position" as used herein is meant a location in the sequence of a protein or peptide. Positions may be numbered sequentially. For example, position 6 is a position of the sixth consecutive residue (counting from N- to C-terminus) in the IgE epitope like peptide. Corresponding positions are determined as outlined below, generally through sequence or structural alignment with other protein or peptide sequences.

"Sequence" means the linear order in which monomers occur in a polymer, for example, the order of amino acids in a polypeptide or the order of nucleotides in a polynucleotide.

"Amino acid" as used herein refers to one of the 20 proteinogenic amino acids or any nonconventional analogues that may be present at a specific, defined peptide, ligand or protein position. The side chain may be in either the L or the D configuration. Amino acids may be referred by either the commonly known three letter symbols or by the one-letter symbols recommended by the IUPAC-IUB Biochemical Nomenclature Commission. (The single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), and Y (Tyr)).

Proteinogenic amino acids are those encoded by the genetic code. Naturally-occurring α-amino acids include, without limitation, alanine (Ala), cysteine (CyS), aspartic acid (Asp), glutamic acid (Glu), phenylalanine (Phe), glycine (Gly), histidine (His), isoleucine (Ile), arginine (Arg), lysine (LyS), leucine (Leu), methionine (Met), asparagine (ASn), proline (Pro), glutamine (Gln), serine (Ser), threonine (Thr), valine (Val), tryptophan (Trp), tyrosine (Tyr). Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr).

The term "nonconventional" amino acids refer to amino acids other than conventional amino acids (i.e., other than proteinogenic). "Nonconventional" amino acids (non-proteinogenic amino acids) may be found in nature or are chemically synthesized. Examples of nonconventional amino acids include, but are not limited to: β-alanine, 3-pyridylalanine, 4-hydroxyproline, O-phosphoserine, N-methylglycine (also known as sarcosine), N-acetylserine, N-formylmethionine, 3-methylhistidine, 5-hydroxylysine, nor-leucine, 1-naphthylalanine (1-nal), 2-naphthylalanine (2-nal), homoserine methylether (Hsm), N-acetylglycine, and other similar amino acids and imino acids.

In the context of the invention it is understood that non-proteinogenic amino acids have the function of amino acid mimetic. Specifically, they have a structure that is different from the general chemical structure of an amino acid included in igE epitope-like peptides of the invention, but they function in a manner similar to a naturally-occurring amino acid of igE epitope-like peptides of the invention.

By "amino acid modification" herein is meant an amino acid substitution, insertion, and/or deletion in a peptide sequence. By "amino acid substitution" or "substitution" herein is meant the replacement of an amino acid at a particular position in a parent peptide sequence with another amino acid.

One of skill in the art will recognize that individual substitutions, additions, or deletions to a peptide or polypeptide sequence which alters, adds, or deletes a single amino acid or a small percentage of amino acids in the encoded sequence is a "conservatively modified variant" where the alteration results in the substitution of an amino acid with a chemically similar amino acid mimetic. The chemically similar amino acid includes, without limitation, a naturally-occurring amino (proteinogenic) acid such as an L-amino acid, a stereoisomer of a naturally occurring amino acid such as a D-amino acid, and a non-conventional (non-proteinogenic) amino acid.

Conservative substitution tables providing functionally similar naturally-occurring amino acids are well known in the art (Creighton, 1993). For example, substitutions may be made within aliphatic amino acids (such as Gly, Ala, le, Leu, Val), where one amino acid is substituted with another member of the group. Substitutions may be made within an aliphatic polar-uncharged group (such as Cys, ser, Thr, Met, Asn, Gln), within amino acids with basic residues (Lys, Arg, His). An amino acid with an acidic side chain, Asp and Glu, may be substituted with its uncharged counterpart, Asn and Gln, respectively; or vice versa. Other exemplary amino acids that are conservative substitutions for one another are as follows: 1) Alanine (Ala), Glycine (Gly); 2) Aspartic acid (Asp), Glutamic acid (Glu); 3) Asparagine (Asn), Glutamine (Gln); 4) Arginine (Arg), Lysine (Lys); 5) Isoleucine (Ile), Leucine (Leu), Methionine (Met), Valine (Val); 6) Phenylalanine (Phe), Tyrosine (Tyr), Tryptophan (Trp); 7) Serine (Ser), Threonine (Thr); and 8) Cysteine (Cys), Methionine (Met).

Less conservative substitutions might involve the replacement of one amino acid by another that has similar characteristics but is somewhat different in size, such as replacement of an alanine by an isoleucine residue. Highly nonconservative replacement might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Such substitutions may involve structures other than the common L-amino acids. Thus, D-amino acids might be substituted for the L-amino acids and yet still be encompassed by the disclosure herein. In addition, non-standard amino acids (i.e., other than the common naturally occurring proteinogenic amino acids) may also be used for substitution purposes to produce similar peptides according to the present invention. If substitutions at more than one position are found to result in a peptide with substantially equivalent or greater binding to allergen-specific IgE, then combinations of those substitutions can be tested to determine if the combined substitutions result in additive or synergistic effects on the binding of the peptide.

The IgE epitope-like peptides of the invention also serve as structural models for non-peptidic compounds with similar biological activity. Those skilled in art recognize that a variety of techniques are available for constructing compounds with the same or similar desired biological activity as the lead peptide. These techniques include replacing the peptide backbone with a backbone composed of phosphonates, amidates, carbamates, sulphonamides, secondary amines and N-methylamino acids.

By "parent peptide" or "parent protein" as used herein is meant a peptide that is subsequently modified to generate a variant. Said parent peptide or protein may be a naturally occurring peptide, or a variant or engineered version of a naturally occurring peptide. Parent peptide may refer to the peptide itself, compositions that comprise the parent peptide, or the corresponding amino acid sequence. Accordingly, by "parent peptide" as used herein is meant a peptide that is modified to generate a variant.

By "variant peptide", "protein variant", "peptide variant", as used herein is meant a peptide sequence that differs from that of a parent peptide sequence by virtue of at least one amino acid modification.

Variant peptide may refer to the peptide itself, a composition comprising the peptide, or the corresponding amino acid sequence.

The term "peptidomimetic" or "peptide mimetic" refers to any synthetic organic molecule that has a three-dimensional structure designed to be substantially similar to a three-dimensional structure of a peptide. Examples of peptidomimetics are, but not limited to, peptoids (polyglycines substituted at amide nitrogen atoms), peptides containing non-standard (i.e., non-proteinogenic) amino acids other than D-amino acids, or conformationally constrained (e.g., cyclized) versions thereof.

"Retro-inverso" modification of naturally occurring polypeptides involves the synthetic assemblage of amino acids with α-carbon stereochemistry opposite to that of the corresponding L-amino acids, i.e. D- or D-allo-amino acids, in reverse order with respect to the native peptide sequence. A "retro-inverso analogue" thus has reversed termini and reversed direction of peptide bonds while approximately maintaining the topology of the side chains as in the native peptide sequence. Accordingly, a "retro inverso analogue" of the ligand of the invention may thus have the following general structure: Z-$X^9$-$X^8$-$X^7$-$X^6$-$X^5$-$X^4$-$X^3$-$X^2$-Arg-Pro-His-$X^1$-U, with Z and U being as defined herein, and $X^1$ to $X^9$ being as defined herein, expect that they are in the D- or D-allo form. Arg, Pro and His are also in the D-form.

"Percentage of sequence identity," as used herein, is determined by comparing two optimally aligned peptide or polypeptide sequences over a comparison window, where the fragment of the amino acid sequence in the comparison window may comprise substitution, a deletion, or an insertion of one or more amino acids as compared to the reference sequence (which does not comprise substitutions, additions or deletions) for optimal alignment of the two sequences.

The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Sequences may be aligned for comparison by using alignment algorithms (Needleman and Wunsch, 1970; Smith and Waterman, 1981), by the search for similarity method (Pearson and Lipman, 1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by manual alignment and visual inspection. The term "substantial sequence identity" between polypeptide sequences refers polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Another indication that two peptides are substantially identical is that the first peptide is immunologically cross-reactive with the antibodies raised against the second peptide. Thus, a peptide is typically substantially identical to a second peptide, for example, where the two peptides differ only by conservative substitutions.

It is understood that in the calculation of sequence identity with respect to any of the polypeptide components set forth herein (as found in residues 1-12 of Structure (I)), the sequence to be compared is taken over the amino acids disclosed therein, irrespective of any N-terminal (i.e., Z) or C-terminal (i.e., U) functionality present. It is further understood that the presence of a stability enhancing moiety covalently linked to the side chain of an amino acid is immaterial to the calculation of sequence identity.

A "stability enhancing moiety" as used herein refers to a moiety to which ligand is covalently attached. Attachments of such moieties affect ligand pharmacokinetics; more specifically they increase ligand's metabolic stability and plasma half-life. Such duration enchaining moieties are, but not limited to, water-soluble polymers, such as polyethylene glycol (PEG), peptide and glycans, or fatty acids. The number of duration enhancing moieties attached may vary; for example, one, two, three, or more identical or different duration enhancing moieties may be attached to the ligand of the invention. Said stability enhancing moiety may also influence (but not limited to) the peptide solubility, gut permeability, resistance to proteases.

It is known to the person skilled in the art that fatty acid conjugates of peptides demonstrate higher stability and longer plasma half-lives (Hackett et al., 2013). A fatty acid is a carboxylic acid with a long aliphatic chain, which is either saturated or unsaturated. Preferably fatty acids have an unbranched chain of an even number of carbon atoms, from 4 to 28. Lipidization is a method by which fatty acids are attached to the peptide. For fatty acid conjugation various approaches are available. Synthesis can be performed where fatty acids are either conjugated to the N-terminus, or to the side-chain of a lysine. Also the cysteine residues in peptides can be modified with fatty acids, giving the corresponding thioester derivatives. The fatty acids that are most commonly used for lipidization are: Caprylic acid (C8), Capric acid (C10), Lauric acid (C12), Myristic acid (C14), Palmitic acid (C16) or Stearic acid (C18).

Covalent attachment of the peptide to polyethylene glycol polymer (PEG) is known to affect peptide pharmacokinetics, more specifically it increases peptide stability and plasma half-life. PEG's most common form is a linear or branched polyether with terminal hydroxyl groups: $HO-(CH_2CH_2O)n-CH_2CH_2-OH$. Monofunctional methoxy-PEG (mPEG) is preferred for peptide modification: $CH_3O-(CH_2CH_2O)n-CH_2CH_2-OH$, as it can be derivatized with a number of linkage moieties, yielding methoxyPEG-amines, -maleimides, or -carboxylic acids. Preferably PEGs of up to 40-50,000 are used in clinical and approved pharmaceutical applications. Two or more lower-weight chains can be added to increase the total molecular weight of the PEG complex. The first step in coupling PEG monomethyl ether to a peptide is to activate mPEG with a functional group. It can be coupled to different available reactive groups on the peptide, such as lysine, aspartic acid, cysteine, glutamic acid, serine, threonine, the N-terminal amine and the C-terminal carboxylic acid or other specific sites.

It is known to the person skilled in the art that introduction of carbohydrate moieties (glycation) also changes the physiological properties of peptides, which can improve their bioavailability. The favourable impact of glycosylation on pharmacokinetic properties of the native peptides leads to an increase in their oral absorption and bioavailability. In addition to O- and N-linked glycosylation approaches, several chemical methods and chemo-enzymatic approaches have been established for the attachment of carbohydrate units to different amino acid residues at the N-terminus of the peptide's sequence (Moradi et al., 2016).

"Antibody" as used herein refers to all types of immunoglobulins, including IgG, IgM, IgA, IgD, and IgE. IgE antibody or immunoglobulin E refers to a type of antibody that has only been found in mammals. The IgE described herein have an essential role in type I hypersensitivity. Hypersensitivity is an abnormally strong response to a stimulus. Immunologically mediated hypersensitivity leading to disease is allergy. Hypersensitivity manifests in various allergy-related conditions such as anaphylaxis, asthma, allergic rhinitis, food allergies, medication allergies, latex allergy, stinging insect allergy and other allergic responses. The antibody typically responsible for an allergic reaction belongs to the IgE isotype. IgE plays a pivotal role in responses to allergens. Allergen is a protein with pro-allergenic prosperities capable of instructing the immune system to start producing IgE antibodies. Development of allergen specific IgE antibodies increased after repeated contact with the allergen is called sensitization.

IgE primes the IgE-mediated allergic response by binding to FcεRI receptors on the surface of effector cells. Effector cells are mast cells and basophils (circulating granulocytes, whose functions overlap with those of mast cells) with high affinity IgE receptors (FcεRI) on the surface; those receptors bind IgE antibodies. Allergen cross-linking of IgE on the surface of effector cells induces aggregation of the FcεRI receptors, leading to the activation, degranulation and the release of mediators of allergic inflammation from the effector cells. The release of mediators leads to allergic reaction and in the worst case to anaphylaxis. Anaphylaxis is a serious, systemic life-threatening allergic reaction. The most common anaphylactic reactions are to food, especially to peanut. Ara h 2 is major peanut allergen. Cross-reactive allergens are members of the same protein family, which can cause allergic reactions by cross-reactivity.

IgE epitope is a part of allergen on to which IgE antibodies bind. IgE paratop is a part of IgE antibody which binds to allergen epitope.

Allergen specific immunotherapy (AIT) is conventionally performed with the administration of increasing amounts of allergens (allergen extracts) to which the patient is sensitized. Adverse events are any allergic reactions to administration of allergen during specific allergen immunotherapy. Those reactions could be local, systemic or anaphylactic.

BRIEF DESCRIPTION OF THE FIGURES

FIG. 1: Schematic presentation of IgE epitope-like peptides of Ara h 2

FIG. 2: A. Binding of IgE epitope-like peptides (ELP 1 to 10) to rabbit Ara h 2 antiserum compared to control wild-type phage. Average and standard deviations from duplicate experiments are shown. B. Individual IgE epitope-like peptides expressed as fusion proteins with pIII protein on the surface of filamentous phage compete for the same binding site with allergen. Black bars: IgE epitope-like peptides expressed on the surface of filamentous phage ($5 \times 10^{10}$ pfu/well) and Ara h 2 (0.25 μg/well). White bars: IgE epitope-like peptides expressed on the surface of filamentous phage ($5 \times 10^{10}$ pfu/well).

DETAILED DESCRIPTION OF THE INVENTION

Figure 3:
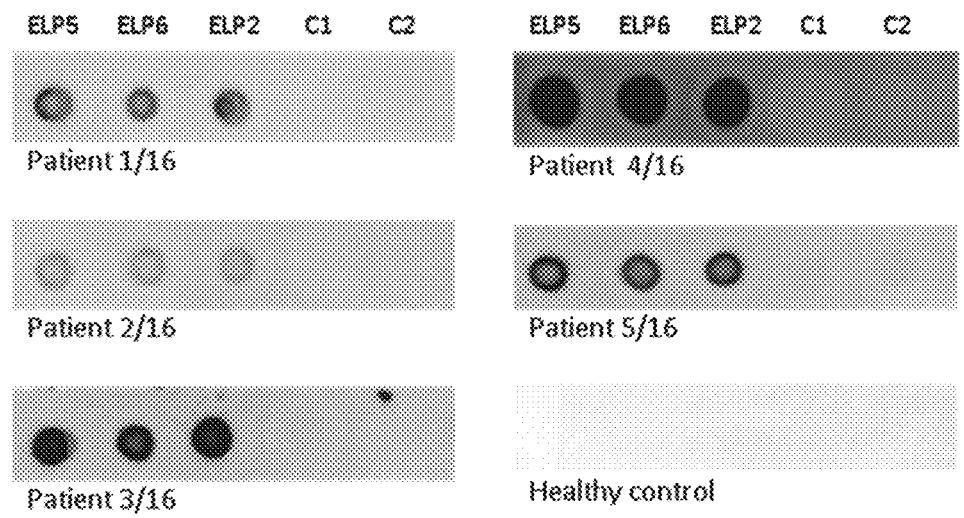
FIG. 3: Recognition of three (ELP 6, ELP 2 and ELP 5) IgE epitope-like peptides by IgE from the serum of five peanut-allergic patients. Labels C1 and C2 correspond to pIII fusions of target-unrelated peptides with an affinity for streptavidin and human leptin, respectively. Healthy control serum is also included.

The "IgE epitope-like peptides" as used herein are peptides that mimic epitopes on allergens onto which IgE antibodies are binding to. The IgE epitope-like peptides bind to antigen-binding site of allergen specific IgEs, do not cross-link allergen specific IgEs on effector cells of allergic patients and do not induce activation and release of mediators of allergic inflammation from effector cells.

The invention further provides IgE epitope-like peptides, discovered by screening of biological peptide libraries. The IgE epitope-like peptides of the invention are binding to peanut and Ara h 2 specific IgEs of peanut allergic patients. They do not cross-link IgEs on basophil and mast cells of the allergic patient and consequently not do induce activation and release of mediators of allergic inflammation from said effector cells. They have the ability to prevent peanut and Ara h 2 allergen IgE cross-linking and thus inhibit mast cell and basophil activation and degranulation in peanut allergic patients.

The IgE epitope-like peptide according to the present invention is a peptide with short chain length, containing a sequence of amino acids or an analogous sequence. Written from amino terminus to carboxy terminus, the peptide of the present invention has the general structure:

$$Z-X^1-His-Pro-Arg-X^2-X^3-X^4-X^5-X^6-X^7-X^8-X^9-U$$

wherein $X^1$ is a polar or charged amino acid, preferably Asp or Asn; $X^2$ s a hydrophobic, aromatic amino acid, preferably Phe or Tyr; $X^3$ may or may not be present, but if present it is a polar or non-polar amino acid, preferably Asn, Ala, Gly, Ser or Pro; $X^4$ may or may not be present, but if present it can be any amino acid, preferably Asp, Arg, Tyr, Pro, Thr, Glu, Leu or Phe; $X^5$ may or may not be present, but if present it is preferably a charged or polar amino acid, and more preferably Ser, Asp or Val; $X^6$ may or may not be present, but if present it is a polar amino acid, preferably Tyr, Ser or Asn; $X^7$ may or may not be present, but if present it is a polar or charged amino acid, preferably Gln, Asn or Asp; $X^8$ may or may not be present, but if present it is a non-polar or polar amino acid, preferably Val, Pro or Ser; $X^9$ may or may not be present, but if present it is a non-polar amino acid, preferably Ala, Trp or Pro; Z is a hydrogen atom replacing the N-terminal amino group or an N-terminal amino group, or a stability enhancing moiety, bound either to the N-terminal amino group or directly to the alpha C-atom of the N-terminal residue; U is a hydrogen atom replacing the C-terminal carboxyl group or a C-terminal carboxyl group, or is a linker or a stability enhancing moiety, bound either to the C-terminal carbonyl group or directly to the alpha C-atom of the C-terminal residue.

According to some embodiments $X^1$ is Asp or Asn.
According to some embodiments $X^1$ is Asp.
According to some embodiments $X^1$ is Asn.
According to some embodiments $X^2$ is Phe or Tyr.
According to some embodiments $X^2$ is Phe.
According to some embodiments $X^2$ is Tyr.
According to some embodiments $X^3$ is not present.
According to some embodiments $X^3$ is present.
According to some embodiments $X^3$ is Asn, Ala, Gly, Ser or Pro.
According to some embodiments $X^3$ is Asn.
According to some embodiments $X^3$ is Ala.
According to some embodiments $X^3$ is Gly.
According to some embodiments $X^3$ is Ser.
According to some embodiments $X^3$ is Pro.
According to some embodiments $X^4$ is not present.
According to some embodiments $X^4$ is present.
According to some embodiments $X^4$ is Asp, Arg, Tyr, Pro, Thr, Glu, Leu or Phe.
According to some embodiments $X^4$ is Asp.
According to some embodiments $X^4$ is Arg.
According to some embodiments $X^4$ is Tyr.
According to some embodiments $X^4$ is Pro.
According to some embodiments $X^4$ is Thr.
According to some embodiments $X^4$ is Glu.
According to some embodiments $X^4$ is Leu.
According to some embodiments $X^4$ is Phe.
According to some embodiments $X^5$ is not present.
According to some embodiments $X^5$ is present.
According to some embodiments $X^5$ is Ser, Asp or Val.
According to some embodiments $X^5$ is Ser.
According to some embodiments $X^5$ is Asp.
According to some embodiments $X^5$ is Val.
According to some embodiments $X^6$ is not present.
According to some embodiments $X^6$ is present.
According to some embodiments $X^6$ is Tyr, Ser or Asn.
According to some embodiments $X^6$ is Tyr.
According to some embodiments $X^6$ is Ser.
According to some embodiments $X^6$ is Asn.
According to some embodiments $X^7$ is not present.
According to some embodiments $X^7$ is present.
According to some embodiments $X^7$ is Gln, Asn or Asp.
According to some embodiments $X^7$ is Gln.
According to some embodiments $X^7$ is Asn.
According to some embodiments $X^7$ is Asp.

According to some embodiments $X^8$ is not present.
According to some embodiments $X^8$ is present.
According to some embodiments $X^8$ is Val, Pro or Ser.
According to some embodiments $X^8$ is Val.
According to some embodiments $X^8$ is Pro.
According to some embodiments $X^8$ is Ser.
According to some embodiments $X^9$ is not present.
According to some embodiments $X^9$ is present.
According to some embodiments $X^9$ is Ala, Pro or Trp.
According to some embodiments $X^9$ is Ala.
According to some embodiments $X^9$ is Pro.
According to some embodiments $X^9$ is Trp.
According to some embodiments Z is a hydrogen atom replacing the N-terminal amino group.
According to some embodiments Z is an N-terminal amino group.
According to some embodiments Z is a stability enhancing moiety, bound either to the N-terminal amino group or directly to the alpha C-atom of the N-terminal residue.
According to some embodiments U is a hydrogen atom replacing the C-terminal carboxyl group.
According to some embodiments U is a C-terminal carboxyl group.
According to some embodiments U is a stability enhancing moiety, bound either to the C-terminal carbonyl group or directly to the alpha C-atom of the C-terminal residue.

The amino acids of said peptide may be in L-form (L-enantiomer), D-form (D-enantiomer), D-form with reverted order (i.e., retro-inverso peptide), combination of both enantiomers or in the form of alpha N-substituted glycine residues forming the corresponding peptoid derivative.

The peptide of the present invention may also be in the form of a peptidomimetic containing non-standard (non-proteinogenic) amino acids or the phosphonate, amidate, carbamate ester or sulphonamide backbone linkages replacing the peptide backbone but retaining the sequences of side chains of the present invention.

The specific examples of the IgE epitope-like peptide of this invention include, but are not limited to, those listed in Table 1.

TABLE 1

Specific examples of the IgE epitope-like peptides

| SEQ ID NO | Amino acid sequence |
|---|---|
| 1 | DHPRFNDSYNSP |
| 2 | DHPRFNRDNDVA |
| 3 | DHPRFNYVSQPW |
| 4 | DHPRFAP |
| 5 | DHPRYGP |
| 6 | DHPRFST |
| 7 | DHPRFAE |
| 8 | DHPRFPL |
| 9 | DHPRFSF |
| 10 | NHPRFNL |

An IgE epitope-like peptide may comprise an amino acid sequence having at least 60%, such as at least 70%, sequence identity with any one of the amino acid sequences SEQ ID NO: 1 to SEQ ID NO: 10.

An IgE epitope-like peptide may comprise an amino acid sequence having at least 80%, such as at least 90%, sequence identity with any one of the amino acid sequences SEQ ID NO: 1 to SEQ ID NO: 10.

An IgE epitope-like peptide may comprise an amino acid sequence having at least 90%, such as at least 95%, sequence identity with any one of the amino acid sequences SEQ ID NO: 1 to SEQ ID NO: 10.

An IgE epitope-like peptide of the present invention may be a variant of a peptide comprising any one of the amino acid sequences SEQ ID NO: 1 to SEQ ID NO: 10, wherein one or more (such as one, two, three, four or five) amino acids in the reference sequence SEQ ID NO: 1 to SEQ ID NO: 10 are substituted by conservative substitutions.

An IgE epitope-like peptide of the present invention may be a variant of a peptide comprising any one of the amino acid sequences SEQ ID NO: 1 to SEQ ID NO: 10, wherein one to five (such as one to three) amino acids in the reference sequence SEQ ID NO: 1 to SEQ ID NO: 10 are substituted by conservative substitutions.

The IgE epitope-like peptides of the present invention bind to peanut and Ara h 2 specific IgEs of peanut allergic patients that are bound on the surface of effector cells. The IgE epitope-like peptides prevent cross-linking of said IgE and thereby prevent degranulation and secretion of mediators of allergic inflammation from said effector cells, after contact with the causative allergen.

The present invention further relates to the pharmaceutical composition comprising an IgE epitope-like peptide of the present invention, and optionally at least one pharmaceutically acceptable excipient.

The at least one pharmaceutically acceptable excipient may be any suitable pharmaceutically acceptable excipient known in the art.

The pharmaceutical composition may be adapted for any suitable route of administration, but preferably is adapted for any of the following routes of administration: oral administration, intramuscular injection, subcutaneous injection, intradermal injection, intravenous injection, intravenous infusion.

The present invention further provides methods for treatment of peanut allergy, for prevention of systemic adverse events during peanut immunotherapy and/or for prevention of allergic reaction during medical interventions with peanut allergen or peanut extracts, said methods comprising administering a therapeutically effective amount of a pharmaceutical composition of the present invention to a patient in need thereof.

The present invention further provides methods for treatment of peanut cross-reactive allergies, for prevention of systemic adverse events during cross-reactive nut immunotherapy and/or for prevention of allergic reaction during medical interventions with cross reactive allergens or allergen extracts, said methods comprising administering a therapeutically effective amount of a pharmaceutical composition of the present invention to a patient in need thereof.

Additionally the invention provides a general method of using IgE epitope-like peptides in the treatment of clinically relevant allergies, for prevention of systemic adverse reactions during specific immunotherapy and/or for prevention of allergic reaction during medical interventions, where IgE epitope-like peptides bind to antigen-binding site of allergen specific IgEs, do not cross-link allergen specific IgEs on effector cells of allergic patients and do not induce activation and release of mediators of allergic inflammation from said effector cells. By binding to antigen-binding site IgE epitope-like peptides prevent the IgE cross-linking by the causative allergen and thus prevent the allergen induced effector cell activation and release of mediators of allergic inflammation in allergic patients.

EXAMPLES

Example 1

IgE Epitope-Like Peptides

Affinity-purified rabbit IgG specific to Ara h 2 was immobilized onto protein G or protein A coupled to Dynabeads (Thermo Fisher Scientific), incubated in 0.5% BSA (Sigma-Aldrich, St. Louis, Missouri, USA) in PBST for 30 min and used as a target in biopanning. Linear dodecamer, linear heptamer and cyclic heptamer random peptide phage libraries (New England Biolabs, Ipswich, Massachusetts, USA) were screened according to the manufacturer's instructions. Briefly, $10^{11}$ plaque forming units were incubated with 15 µL of immobilized Dynabeads for 1 h at room temperature. Unbound phages were washed with PBST. Bound phages were eluted either specifically with Ara h 2 or non-specifically with 0.1 M glycine buffer with pH 2.2 and amplified in the *Escherichia coli* K12 ER2738 to be used in the next rounds of biopanning. After the third round, *E. coli* were infected with the eluted phages and grown on LB plates containing 5-bromo-4-chloro-3-indolyl-β-D-galactopyranoside and isopropyl β-D-1-thiogalactopyranoside. The plates were incubated overnight at 37° C. Individual plaques were picked for each type of phage library used and amplified. The DNA from the phage clones were isolated and sequenced to determine the displayed peptide primary structure. SEQ ID, name and amino acid sequence of representative IgE epitope-like peptides identified by screening peptide libraries are shown in FIG. 1 A. General structure of IgE epitope-like peptides is shown on FIG. 1B.

Example 2

Binding of the IgE Epitope-Like Peptides to Anti Ara h 2 Rabbit Antiserum

Individual IgE epitope-like peptides expressed as fusion proteins with pIII protein on the surface of filamentous phage were evaluated for their binding to anti Ara h 2 rabbit antiserum (INDOOR Biotechnologies, Charlottesville, Virginia, USA) in duplicates with ELISA. The wells of the microtiter plates were coated overnight at 4° C. with Ara h 2 rabbit antiserum diluted to 1:1000 in 0.1 M NaHCO3 (pH 8.6). The wells were blocked with 5% skim milk in PBS and washed with PBST. Next, 100 µL equal amount ($5 \times 10^{10}$ pfu/well) of phages was added and incubated for 1 h at room temperature. For detection, mice anti-M13 monoclonal antibodies conjugated with HRP (GE Healthcare, Little Chalfont, UK) diluted to 1:5000 were incubated for 1 h at room temperature and the TMB Super Tracker (ImmunoO4) with added 0.006% $H_2O_2$ was used as a substrate. The reaction was terminated with 2 M $H_2SO_4$, and the absorbance was measured at 450 nm with a microtiter plate reader. The results show, that IgE epitope-like peptides bind to anti Ara h 2 rabbit antiserum.

Purified phage clones ($5 \times 10^{10}$ pfu/well) and Ara h 2 (0.25 µg/well) were added to microtiter plate wells coated with Ara h 2 rabbit antiserum, blocked (as above) and allowed to compete for the target antibody binding site. After 1 h of incubation at room temperature, anti-M13 monoclonal antibodies conjugated with HRP (GE Healthcare) diluted to 1:5,000 were added. Detection was performed as above. The results show that individual IgE epitope-like peptides expressed as fusion proteins with pIII protein on the surface of filamentous phage compete for the same binding site with allergen.

Example 3

Binding of IgE Epitope-Like Peptides to IgE of Peanut Allergic Patients

Three selected IgE epitope-like peptides (ELP 2, ELP 5, ELP 6) were extracted as recombinant fusions with bacteriophage minor coat protein pIII from the periplasm of host bacteria with osmotic shock. Two target-unrelated control peptides also fused to protein pIII (binders to streptavidin and human leptin) were extracted in the same way and served as negative controls (C1, C2). Briefly, *E. coli* host bacteria were infected with individual phage clones and grown for 2 hours at 37° C. with agitation. Bacteria pellets were spun down at 5000×g for 10 min and resuspended in 1 ml of an ice-cold solution consisting of 20% sucrose, 200 mM Tris-HCl pH 8.0 and 1 mM EDTA supplemented with protease inhibitor cocktail (EZBlock™, BioVision, San Francisco, USA) at a dilution of 1:200. After 1 h incubation on ice with occasional stirring supernatants were harvested by centrifugation at 12000×g for 20 minutes at 4° C. Resulting periplasmic extracts containing peptide-pII fusion proteins were concentrated (4-5 fold) and sucrose buffer exchanged for PBS by ultrafiltration with 10 kDa cut-off membrane (Microsep Advance Centrifugal Device, Pall Corporation, New York, USA). For immunoprecipitation of each selected peptide, 20 µg of affinity purified rabbit IgG against Ara h 2 (INDOOR Biotechnologies, Charlottesville, Virginia, USA) were covalently coupled to 1 mg of Dynabeads M-280 Tosylactivated™ (Thermo Fisher Scientific) according to manufacturer's protocol. Control peptides were immunoprecipitated in the same way using 10 µg of anti-human leptin antibody (R and D Systems Cat #MAB398 RRID:AB_2136056) coupled to 1 mg of Dynabeads M-280 Tosylactivated™ in the case of peptide with the affinity toward human leptin and 0.5 mg of streptavidin-coupled beads (Dynabeads™ MyOne™ Streptavidin T1, Thermofisher Scientific) in the case of peptide with the affinity towards streptavidin. After the concentrated periplasmic extracts containing pIII-fusion proteins were incubated with respective beads for 1 h at room temperature under agitation, the beads were washed three times with 0.01 M Na-phosphate (pH 7.4) and captured fusion proteins eluted in 25 µl glycine-HCl (pH 2.5) following immediate neutralization with 1 M Tris (pH 8.0).

Immunodot assay: 2 µl of each sample containing 200 µg of IgE epitope-like peptides (ELP 2, ELP 5, ELP 6)-pIII fusion proteins were spotted onto a 0.45 µm nitrocellulose membrane (GE Healthcare). The membrane was blocked with 5% skimmed milk in Tris-buffered saline/0.05% Tween 20 (TBST) for 3 hours at room temperature. Following washing, the membrane was incubated with a sera pool (patients 1-9) or with individual serum (patients 1 to 12) diluted to 1:10 in 0.05% TBST overnight at 4° C. Membranes were washed three times with 0.1% TBST and incubated with HRP-conjugated goat anti-human IgE antibodies (RRID: AB_2535570) diluted to 1:2000 in 1% BSA/ 0.1% TBST for 2 h at room temperature. The reactive dots were visualized with CCD image analysis system (G-Box, Syngene, United Kingdom) after 5 minutes incubation in SuperSignal West Dura Extended Duration Substrate (Thermo Fisher Scientific). The results show that IgE epitope-like peptides (ELP 2, ELP 5, ELP 6) bind to patients' IgE (FIG. 3).

Example 4

IgE Epitope-Like Peptides Showing No Allergenic Activity

Figure 4:
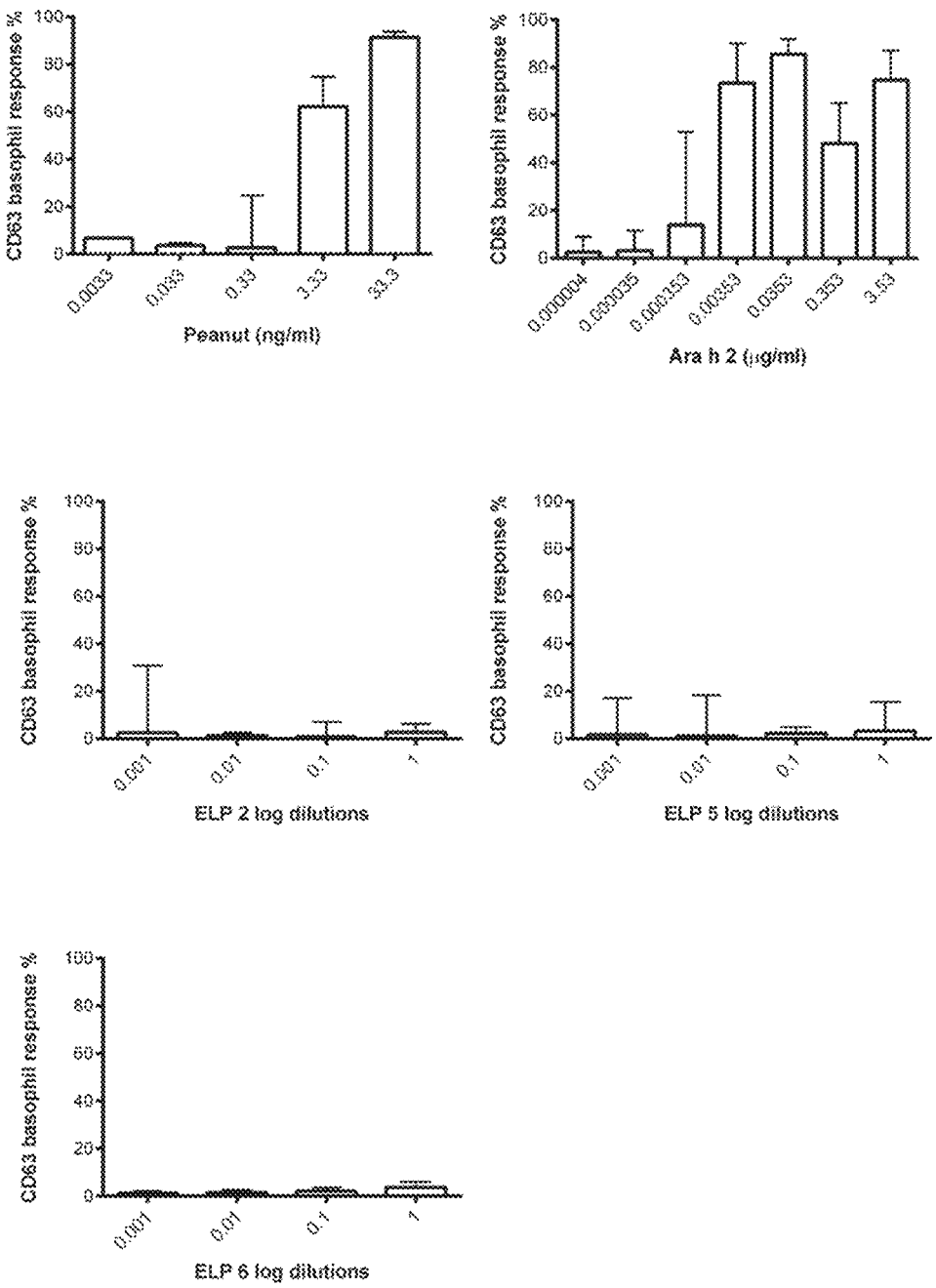
FIG. 4: Basophil CD63 response after stimulation with peanut extract, Ara h 2 or specific IgE epitope-like peptides L12-N14, L7-N40 and L7-N48 in five peanut allergic patients. Data are presented as median and IQR.

Basophil Activation Assay (BAT) was performed on the heparinized whole blood incubated with basophil stimulation buffer with IL-3 (Buhlmann, Switzerland) containing fMLP (50 µg/ml; Sigmal Aldrich, Germany), anti-FceRI mAbs (550 ng/ml; Buhlmann), peanut extract (33.3-0.333 ng/ml), Ara h2 (3.53-0.353×10-7 µg/ml; Indoor Biotechnologies, UK), and individual synthetic IgE epitope-like peptides (L12-N14, L7-N40 and L7-N48) (1-0.001 mg/ml; EZBiolab, CA USA) at 37° C. for 15 minutes. Degranulation was stopped by chilling on ice, after which anti-CD63, anti-CD123, and anti-HLA-DR mAb (BD Biosciences, USA) were added and incubated for 20 minutes. Finally, whole blood probes were lysed, washed, fixed, and analyzed within 2 hours on a FACSCanto II flow cytometer (BD Biosciences). IgE epitope-like peptides showed no allergenic activity, compared to peanut extract or Ara h 2 (FIG. 4).

Example 5

Blocking of Allergenic Activity of Ara h 2 by IgE Epitope-Like Peptides

Figure 5:
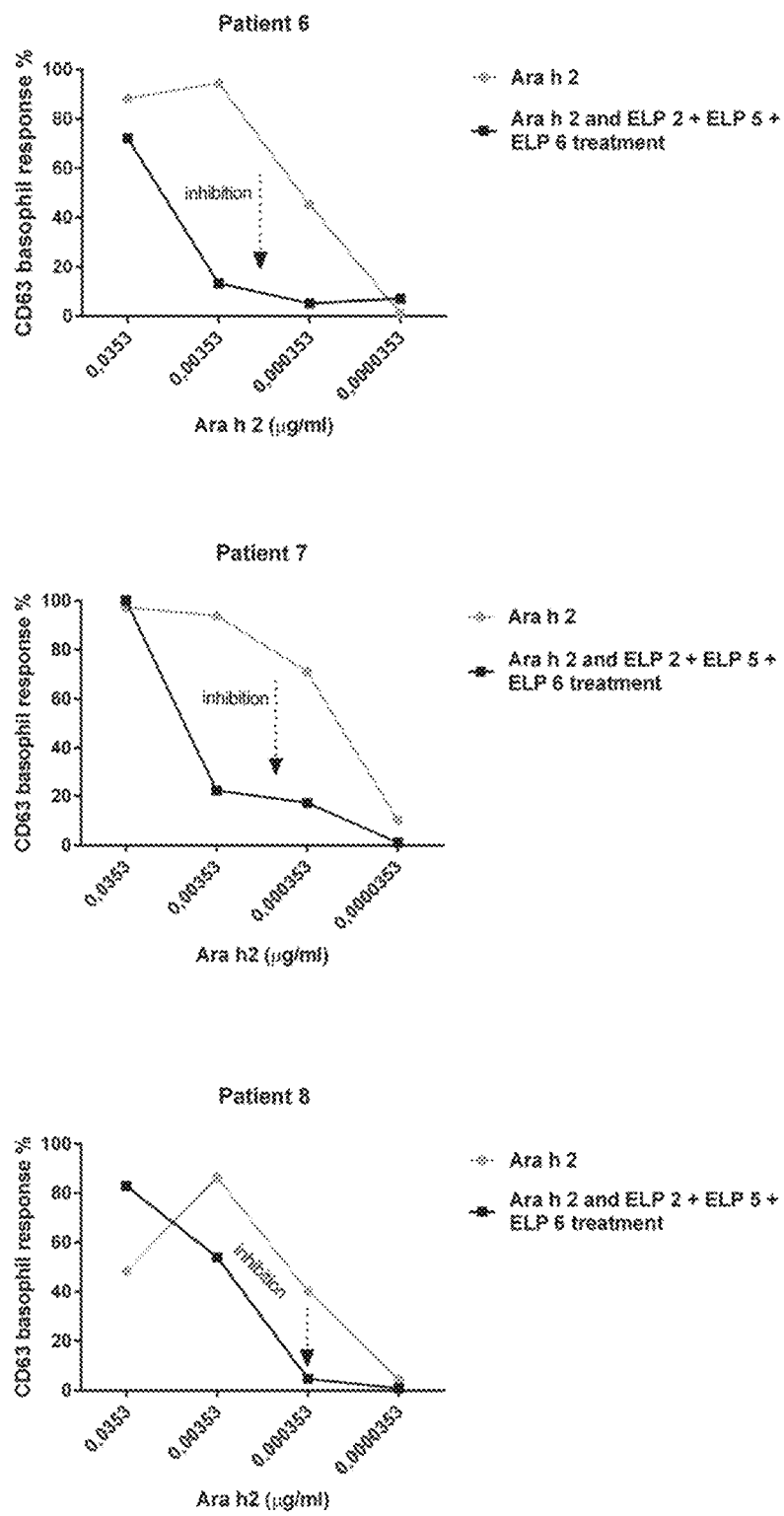
FIG. 5: Inhibition of basophil CD63 response to Ara h 2 stimulation after the treatment with specific IgE epitope-like peptides L12-N14, L7-N40 and L7-N48 in three peanut allergic patients.

Inhibition of Ara h 2 induced basophil activation by IgE epitope-like peptides. Basophil Activation Assay (BAT) was performed on the heparinized whole blood incubated with mixture of all three free synthetic IgE epitope-like peptides (L12-N14, L7-N40 and L7-N48) in the final concentration 50 µg/ml for 15 minutes at 37° C. Afterwards, Ara h2 in the final concentration of $3.5 \times 10^{-2}$-$3.5 \times 10^{-5}$ µg/ml was added and samples were incubated for another 15 min at 37° C. Degranulation was stopped by chilling on ice, after anti-CD64/anti-CD123/anti-HLA-DR mAb were added and incubated for 20 min. Finally, whole blood probes were lysed, washed, fixed, and analyzed within 2 hours on a FACSCanto II flow cytometer (BD Biosciences). The results of BAT inhibition with IgE epitope-like peptides were compared to the results of BAT at same final concentrations of Ara h2. The results show that IgE epitope-like peptides markedly reduce allergenic activity of Ara h 2 (FIG. 5).

REFERENCES

Akdis, M., 2014. New treatments for allergen immunotherapy. World Allergy Organ J 7, 23.

Asarnoj, A., Moverare, R., Ostblom, E., Poorafshar, M., Lilja, G., Hedlin, G., van Hage, M., Ahlstedt, S., Wickman, M., 2010. IgE to peanut allergen components: relation to peanut symptoms and pollen sensitization in 8-year-olds. Allergy 65, 1189-1195.

Berings, M., Karaaslan, C., Altunbulakli, C., Gevaert, P., Akdis, M., Bachert, C., Akdis, C. A., 2017. Advances and highlights in allergen immunotherapy: On the way to sustained clinical and immunologic tolerance. J Allergy Clin Immunol 140, 1250-1267.

Bock, S. A., Munoz-Furlong, A., Sampson, H. A., 2001. Fatalities due to anaphylactic reactions to foods. J Allergy Clin Immun 107, 191-193.

Calderon, M. A., Demoly, P., Gerth van Wijk, R., Bousquet, J., Sheikh, A., Frew, A., Scadding, G., Bachert, C., Malling, H. J., Valenta, R., Bilo, B., Nieto, A., Akdis, C., Just, J., Vidal, C., Varga, E. M., Alvarez-Cuesta, E., Bohle, B., Bufe, A., Canonica, W. G., Cardona, V., Dahl, R., Didier, A., Durham, S. R., Eng, P., Fernandez-Rivas, M., Jacobsen, L., Jutel, M., Kleine-Tebbe, J., Klimek, L., Lotvall, J., Moreno, C., Mosges, R., Muraro, A., Niggemann, B., Pajno, G., Passalacqua, G., Pfaar, O., Rak, S., Senna, G., Senti, G., Valovirta, E., van Hage, M., Virchow, J. C., Wahn, U., Papadopoulos, N., 2012. EAACI: A European Declaration on Immunotherapy. Designing the future of allergen specific immunotherapy. Clin Transl Allergy 2, 20.

Cornelius, C., Schoneweis, K., Georgi, F., Weber, M., Niederberger, V., Zieglmayer, P., Niespodziana, K., Trauner, M., Hofer, H., Urban, S., Valenta, R., 2016. Immunotherapy With the PreS-based Grass Pollen Allergy Vaccine BM32 Induces Antibody Responses Protecting Against Hepatitis B Infection. EBioMedicine 11, 58-67.

Creighton, T. E., 1993. Proteins: Structures and Molecular Properties. W. H. Freeman.

Gernez, Y., Nowak-Wegrzyn, A., 2017. Immunotherapy for Food Allergy: Are We There Yet? J Aller C Imm-Pract 5, 250-272.

Hackett, M. J., Zaro, J. L., Shen, W. C., Guley, P. C., Cho, M. J., 2013. Fatty acids as therapeutic auxiliaries for oral and parenteral formulations. Adv Drug Deliv Rev 65, 1331-1339.

Larche, M., 2011. T cell epitope-based allergy vaccines. Curr Top Microbiol Immunol 352, 107-119.

Linhart, B., Valenta, R., 2012. Mechanisms underlying allergy vaccination with recombinant hypoallergenic allergen derivatives. Vaccine 30, 4328-4335.

MacGinnitie, A. J., Rachid, R., Gragg, H., Little, S. V., Lakin, P., Cianferoni, A., Heimall, J., Makhija, M., Robison, R., Chinthrajah, R. S., Lee, J., Lebovidge, J., Dominguez, T., Rooney, C., Lewis, M. O., Koss, J., Burke-Roberts, E., Chin, K., Logvinenko, T., Pongracic, J. A., Umetsu, D. T., Spergel, J., Nadeau, K. C., Schneider, L. C., 2017. Omalizumab facilitates rapid oral desensitization for peanut allergy. J Allergy Clin Immunol 139, 873-881 e878.

Moradi, S. V., Hussein, W. M., Varamini, P., Simerska, P., Toth, I., 2016. Glycosylation, an effective synthetic strategy to improve the bioavailability of therapeutic peptides. Chem Sci 7, 2492-2500.

Needleman, S. B., Wunsch, C. D., 1970. A general method applicable to the search for similarities in the amino acid sequence of two proteins. J Mol Biol 48, 443-453.

Pearson, W. R., Lipman, D. J., 1988. Improved tools for biological sequence comparison. Proc Natl Acad Sci USA 85, 2444-2448.

Prescott, S. L., Pawankar, R., Allen, K. J., Campbell, D. E., Sinn, J., Fiocchi, A., Ebisawa, M., Sampson, H. A., Beyer, K., Lee, B. W., 2013. A global survey of changing patterns of food allergy burden in children. World Allergy Organ J 6, 21.

Smith, T. F., Waterman, M. S., 1981. Comparison of biosequences. Adv Appl Math 2, 482-489.

Valenta, R., Campana, R., Marth, K., van Hage, M., 2012. Allergen-specific immunotherapy: from therapeutic vaccines to prophylactic approaches. J Intern Med 272, 144-157.

Valenta, R., Campana, R., Niederberger, V., 2017. Recombinant allergy vaccines based on allergen-derived B cell epitopes. Immunol Lett 189, 19-26.

The invention claimed is:

1. A method for treatment of peanut allergy, for prevention of systemic adverse events during peanut immunotherapy or for prevention of allergic reaction during medical interventions with peanut allergens or peanut extracts, said method comprising administering a therapeutic effective amount of a pharmaceutical composition comprising:

at least one peptide having the following structure:

$$Z\text{-}X1\text{-}His\text{-}Pro\text{-}Arg\text{-}X2\text{-}X3\text{-}X4\text{-}X5\text{-}X6\text{-}X7\text{-}X8\text{-}X9\text{-}U \quad \text{(Structure I)}$$

wherein:
X1 is a polar or charged amino acid: X2 is a hydrophobic, aromatic amino acid;
X3 may or may not be present, but if present it is a polar or non-polar amino acid;
X4 may or may not be present, but if present it can be any amino acid;
X5 may or may not be present, but if present it is a charged or polar amino acid;
X6 may or may not be present, but if present it is a polar amino acid;
X7 may or may not be present, but if present it is a polar or charged amino acid;
X8 may or may not be present, but if present it is a non-polar or polar amino acid;
X9 may or may not be present, but if present it is a non-polar amino acid;
Z is a hydrogen atom replacing the N-terminal amino group or an N-terminal amino group, or a stability enhancing moiety, bound either to the N-terminal amino group or directly to the alpha C-atom of the N-terminal residue;
U is a hydrogen atom replacing the C-terminal carboxyl group or a C-terminal carboxyl group, or is a linker or a stability enhancing moiety, bound either to the C-terminal carbonyl group or directly to the alpha C-atom of the C-terminal residue, or the retro-inverso analogue of the peptide, and optionally at least one pharmaceutically acceptable excipient,
wherein the at least one peptide is selected from the group consisting of SEQ ID NO: 1-10.

* * * * *